United States Patent [19]

Tickner

[11] 4,265,251
[45] May 5, 1981

[54] METHOD OF DETERMINING PRESSURE WITHIN LIQUID CONTAINING VESSEL

[75] Inventor: Ernest G. Tickner, Morgan Hill, Calif.

[73] Assignee: Rasor Associates, Inc., Sunnyvale, Calif.

[21] Appl. No.: 52,745

[22] Filed: Jun. 28, 1979

[51] Int. Cl.³ .................................................. A61B 5/02
[52] U.S. Cl. .................................. 128/660; 128/662; 128/663; 73/703
[58] Field of Search ............................. 128/661–663, 128/672–673, 660; 73/703, 700, 861.25

[56] References Cited

U.S. PATENT DOCUMENTS

| | | | |
|---|---|---|---|
| 3,640,271 | 2/1972 | Horton | 128/662 |
| 3,937,668 | 2/1976 | Zolle | 424/1 |

OTHER PUBLICATIONS

Tickner, E. G. et al., "Non-Invasive Assessment of Pulmonary Hypertension Using the Bubble UTS Resonance Pressure (BURP) Method", Nat. Tech. Inf. Service Rept. No. HR-62917-1A, Apr. 1977.
Fairbank, W. M. et al., "A New Non-Invasive Technique for Cardiac Pressure Measurement: Resonant Scattering of Ultrasound from Bubbles", IEEE Transactions on Biomed. Engr., vol. BME-24, No. 2, Mar. 1977, pp. 107–110.
Feigenbaum, H. et al., "Indentification of Ultrasound Echoes from the LV by Intracardiac Inj. of Indocyanine Green", Circulation vol. XLI, Apr. 1970, pp. 615–621.

*Primary Examiner*—Robert W. Michell
*Assistant Examiner*—Francis J. Jaworski
*Attorney, Agent, or Firm*—Phillips, Moore, Weissenberger, Lempio & Majestic

[57] ABSTRACT

Pressure within a liquid containing vessel is determined by adding a solid precursor for at least one bubble to the liquid, retaining the precursor in the liquid for a sufficient time for it to form at least one bubble and generate a sonic signal, metering a characteristic of the sonic signal which is representative of the pressure in the liquid and determining the pressure in the liquid from the measured characteristic.

9 Claims, 4 Drawing Figures

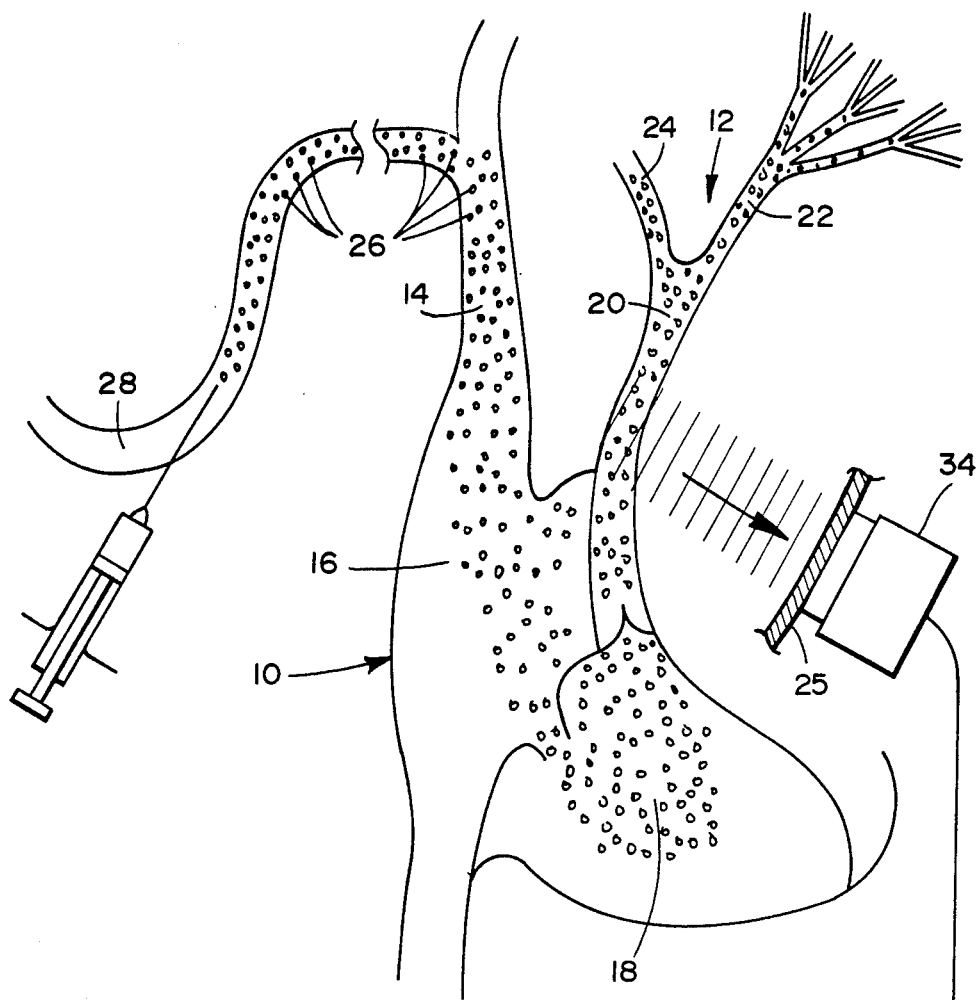
FIG. 1
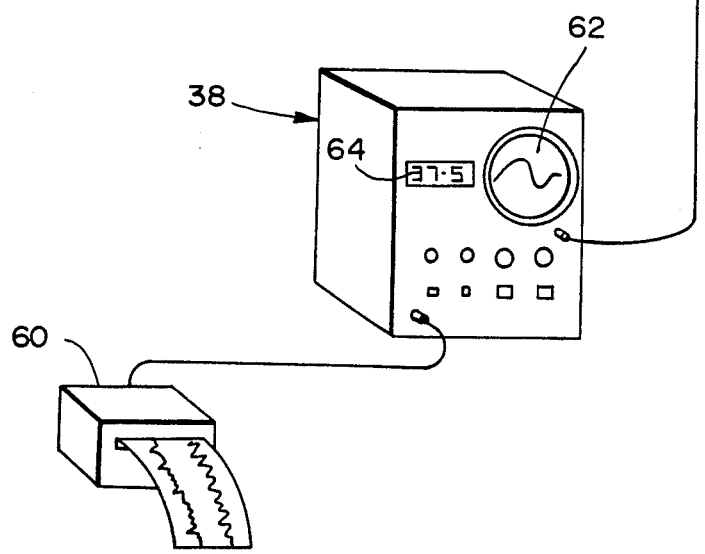

METHOD OF DETERMINING PRESSURE WITHIN LIQUID CONTAINING VESSEL

BACKGROUND OF THE INVENTION

1. Field of the Invention

The invention relates to the measurement of pressure within a liquid containing vessel. More particularly, the invention relates to a method for measuring pressure within the cardiovascular system of a living test subject.

2. Prior Art

The measurement of pressure within a liquid containing vessel such as the cardiovascular system of a living being can be performed by any of a number of methods. Catheterization and direct measurement of pressure is one wholly accurate method. Systemic blood pressure may also be measured externally of the test subject as by attaching a blood pressure cuff about a portion of the subject's body and listening for Korotkoff sounds, measuring the Doppler shift of the artery wall with fluctuating pressure, measuring the derivative of the instantaneous pressure at the cuff, and the like. Other methods of making such blood pressure determinations are discussed in, for example, "The Direct and Indirect Measurement of Blood Pressure" by L. A. Geddes, Yearbook Medical Publishers, Inc., Chicago, Ill., 1970.

The direct catherization method of measuring blood pressure has the advantage of being useable any place within the cardiovascular system, to the extent that irreversible physical damage and shock is not caused by the catheterization technique. The various techniques which require the use of a cuff can generally be used only on parts of the body where the cuff can be readily attached, for example, an arm, a leg, a finger, or the like. And, this approach is only amenable to the systemic circulation, for example, it cannot be used to measure pulmonic arterial pressure. Further, with small infants such as premature babies, it may be impossible, at times, to properly attach such a cuff. Hence, these techniques, while finding wide usefulness, are not useful to provide certain desired data such as the differences in blood pressure in different portions of the cardiovascular system, and the measurement of blood pressures in small infants, although the latter can be accomplished, at times, with special cuffs.

An attempt has previously been made to utilize the fact that when ultrasonic signals are reflected from microbubbles of known size, the frequency of the reflected signal will be a function of the pressure in the liquid in which the bubbles exist. If such bubbles are in a cardiovascular system of a living being, the frequency of the reflected signals from the bubbles will vary over a heartbeat in response to the variation in pressure within the cardiovascular system. This technique has been found, however, to be difficult to practice, because the ultrasonic signals have set up standing waves with the microbubbles, at times, at a node, and because the frequency of the signals has needed to be swept, which in combination with the existence of standing wave nodes has led to the detection of false signals. Thus, while one has been able in the past to inject preformed microbubbles into the cardiovascular system, and to reflect ultrasonic signals from these bubbles as they pass a desired position in that system, for example, the main pulmonary artery, the ultrasonic reflection system has not provided a signal which as a practical matter can be utilized for accurate measurements of blood pressure.

It is also known, as set out in copending U.S. Pat. application Ser. No. 36,098, of E. Glenn Tickner and Ned S. Rasor, to measure instantaneous blood flow rate in a cardiovascular system using microbubbles of uniform size in the system and to enhance ultrasonic images by injection of such microbubbles.

It would be highly desirable to provide a method for measuring pressure within a liquid containing vessel, particularly within the cardiovascular system of a living being, which method could measure the pressure in the system at different points therein and could be readily utilized with infants as well as adults. It would particularly be advantageous if such a system would allow measurement of pressure within the heart itself, without the necessity of performing a relatively risky catheterization and insertion of a pressure detector into the heart from a vein or artery. It would also be useful if blood flow rate and/or ultrasonic image enhancement could be provided with particularly advantageous signal-to-noise ratios.

SUMMARY OF THE INVENTION

The invention relates to a method of determining the pressure within a liquid containing vessel. As a first step, a solid precursor for at least one bubble is added to the liquid. The precursor is retained in the liquid for a sufficient time to form at least one bubble and to generate a sonic signal. A characteristic of the sonic signal which is representative of the pressure in the liquid is measured. Thereafter, the pressure in the liquid is determined from the measured characteristic.

The invention provides a very advantageous method for measuring pressure within the cardiovascular system of a living being. This method is also useful with other liquid containing vessels without modification thereof.

BRIEF DESCRIPTION OF THE DRAWINGS

The invention will be better understood by reference to the figures of the drawing wherein like numbers denote like parts throughout and wherein:

FIG. 1 illustrates, schematically, operation of an embodiment in accordance with the present invention;

DETAILED DESCRIPTION OF THE PREFERRED EMBODIMENT

Figure 2:
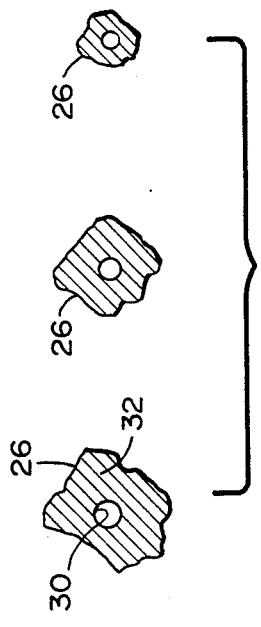
FIG. 2 illustrates microbubble generating material useful in a method in accordance with the present invention.

Adverting to FIG. 1, there is shown therein in a generally schematic representation a heart 10 which forms a portion of a cardiovascular system 12, part of which is shown in FIG. 1, of a living test subject. In the representation of FIG. 1, blood flows from the superior vena cava 14 into the right atrium 16, then into the right ventricle 18, on to the main pulmonary artery 20, and then on via the left pulmonary artery 22 and the right pulmonary artery 24 to the remainder of the cardiovascular system 12.

In accordance with the present invention a solid bubble precursor, such as the various particles 26 seen in FIGS. 1 and 2, are added to the blood 28 which fills the cardiovascular system 12. These particles 26 are carried along with the blood flow in the manner just described. Generally the particles 26 would be injected into the blood stream a slight distance upstream of the heart 10 and then would be carried therethrough by the blood flow.

The particles 26 serve as microbubble precursors in a method which will be explained. The term "bubble" is used to denote bubbles of any size. The term "microbubble" as used herein refers to bubbles which generate ultrasonic signals on their formation. Briefly, the solid microbubble precursors or particles 26 will generally comprise a hollow interior space 30 (See FIG. 2) completely enclosed therein by an outer surrounding wall 32. The outer surrounding wall will generally be of a saccharide composition. A particular preferred composition is approximately 80% sucrose and 20% lactose. The hollow space 30 will generally be filled with a gas which is of a pressure above the pressure which exists within the cardiovascular system 18. Such compositions as have just been described for the particles 26 can be formed generally as described in U.S. Pat. No. 3,012,893, issued Dec. 12, 1961 to L. Kremzner and W. A. Mitchell. It is important to the present invention, however, that the amount of gas in the hollow space 30 of each one of the particles 26 of the present invention be generally the same so that when the outer wall 32 of each particle 26 dissolves sufficiently to allow the gas to escape from the hollow space 30, the resulting microbubbles formed in the cardiovascular system will be of a uniform size. FIG. 2 shows the particles 26 dissolving as they flow from left to right in the cardiovascular system.

Figure 3:
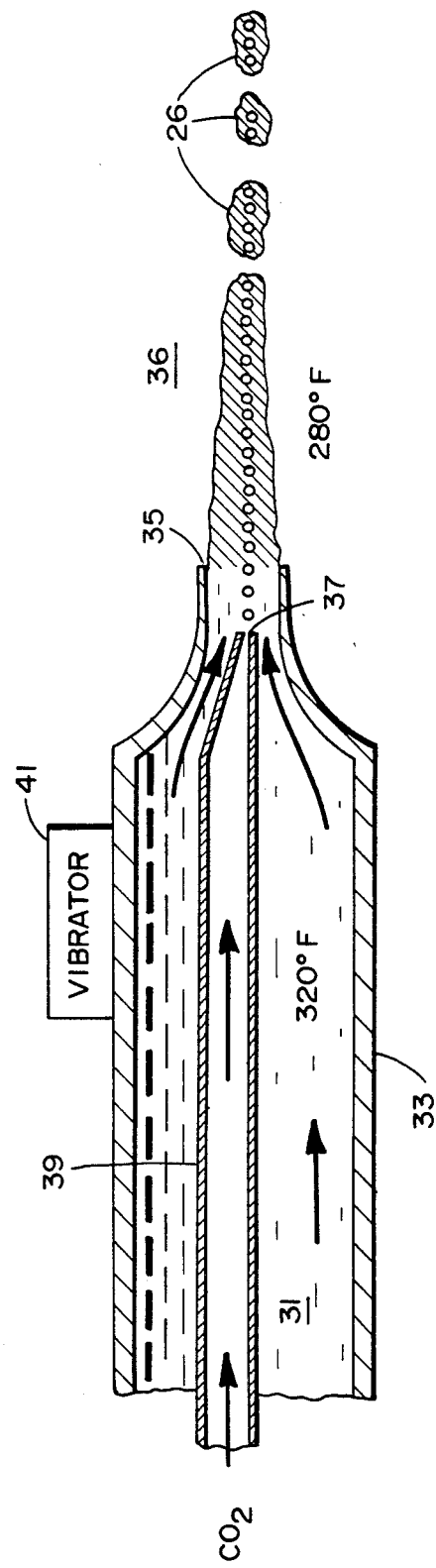
FIG. 3 illustrates formation of microbubble generating material useful in the practice of the present invention.

It has been found that if particles 26 are made in accordance with the teachings of the aforementioned U.S. Pat. No. 3,012,893, sufficient uniformity of amount of gas entrapped in the hollow space 30 is not attained. However, it also has been found that if a viscous sugar solution 31, of the composition set out in that patent, is flowed through a tube 33 as shown in FIG. 3, with the temperature of the sugar solution being held just a few degrees above the solidification point thereof, and if an end 35 of the tube exits into a pressurized cooled zone 36 which is at a temperature below the solidification temperature of the viscous sugar liquid, and if a gas such as carbon dioxide is introduced generally centrally into the flowing liquid via a capillary tube 39, with an end 37 of the capillary tube 39 being at or near an end 35 of the tube 33, then as the sugar quickly solidifies, the amount of carbon dioxide or other gas trapped in each of the resulting quickly solidified microbubble precursor, or particles, 26 is substantially equal. Generally, the entire apparatus is kept at a elevated pressure, for example 5 to 50 atmospheres. A vibrator 41 is placed adjacent the tube 33 to create dynamic (Rayleigh) instability whereby particles 26 are produced having as few as possible hollow spaces 30 per particle. Generally, about thirty hollow spaces 30 have been formed per particle 26, although less, most preferably one, is preferred.

Generally, the amount of gas entrapped within each one of the particles 26 is controlled so that when a microbubble is produced therefrom, it will be generally within a range from about 325 microns to about 0.5 micron in diameter. More preferably, the microbubbles would have a diameter below about 150 microns and above about 1.0 micron. Microbubbles of about 25 microns in size have been found to be very suitable for use in the method of the present invention.

The particles 26 can be added to the cardiovascular system over a period of time, if desired, so as to provide measurements of blood pressure over one or more heartbeats. Further, the microbubble precursor 26 can be added as a particle containing several microbubbles therein, which particle may be broken up by the agitation action occurring within the heart 10. Generally, however, it would be preferable to use a plurality of particles 26, each of which contains, generally, a single hollow space 30 filled with an equal quantity of gas. Large aggregates of precursor 26 can be ground up to provide smaller particles having only one or a few hollow spaces 30, or particles 26 can be used having up to about fifty such hollow spaces 30. It is noted that even if all of the particles 26 are added at a single time, their time of arrival at any particular position in the cardiovascular system 12 will generally not be quite identical because of the agitation taking place within the heart 10 and other portions of the cardiovascular system 12.

The particles 26 are retained in the blood 28 for a sufficient time to form the desired microbubbles. On formation of a microbubble, a transient ultrasonic signal having a large amplitude is generated since the microbubble expands outwardly very rapidly and alternately contracts and expands until it attains its equilibrium size and shape at the lesser pressure which exists within the cardiovascular system 12, as compared with the higher pressure within the hollow space 30. The ultrasonic signal is then generated by this alternate expansion and contraction (compression wave).

It follows that a plurality of ultrasonic signals are generated as a function of time as the various microbubbles are formed on dissolving of the various particles 26 or on dissolving of portions thereof.

A characteristic of the ultrasonic signal which is generated is measured, which characteristic is representative of the pressure in the blood 28. In accordance with the present invention, this characteristic is generally the frequency of the ultrasonic signal which has been generated. Normally, a measurement will be made of the frequency generated by the formation of the microbubbles as a function of time. From this measurement, the pressure in the blood 28 is determined.

Basically, the ultrasonic signal generated is picked up by an ultrasonic sensitive transducer 34 attached to a living being opposite the position at which the particles 26 are dissolving. In the particular embodiment shown in FIG. 1, the transducer 34 is on the chest 25 of the test subject generally opposite the main pulmonary artery and the pressure being determined is that within the main pulmonary artery.

Briefly, as each microbubble is formed by dissolving of at least part of the wall 32 to expose the hollow space 30 or as the wall 32 thins sufficiently to cause the pressurized bubble 30 to fracture it, the microbubble expands to beyond its equilibrium size then contracts to below its equilibrium size, and alternately expands and contracts until it finally attains substantially its equilibrium size and shape. The frequency of the signal thereby detected by the transducer 34 is a function of the pressure in the cardiovascular system 12 opposite the positioning of the transducer 34. Briefly, the pressure is directly proportional to the frequency as detected. The output from the transducer 34 is conventionally converted from a frequency versus time representation to a voltage versus time representation. In the simplest instance, this would be via analog signal processing means 38 as shown in FIG. 4.

Figure 4:
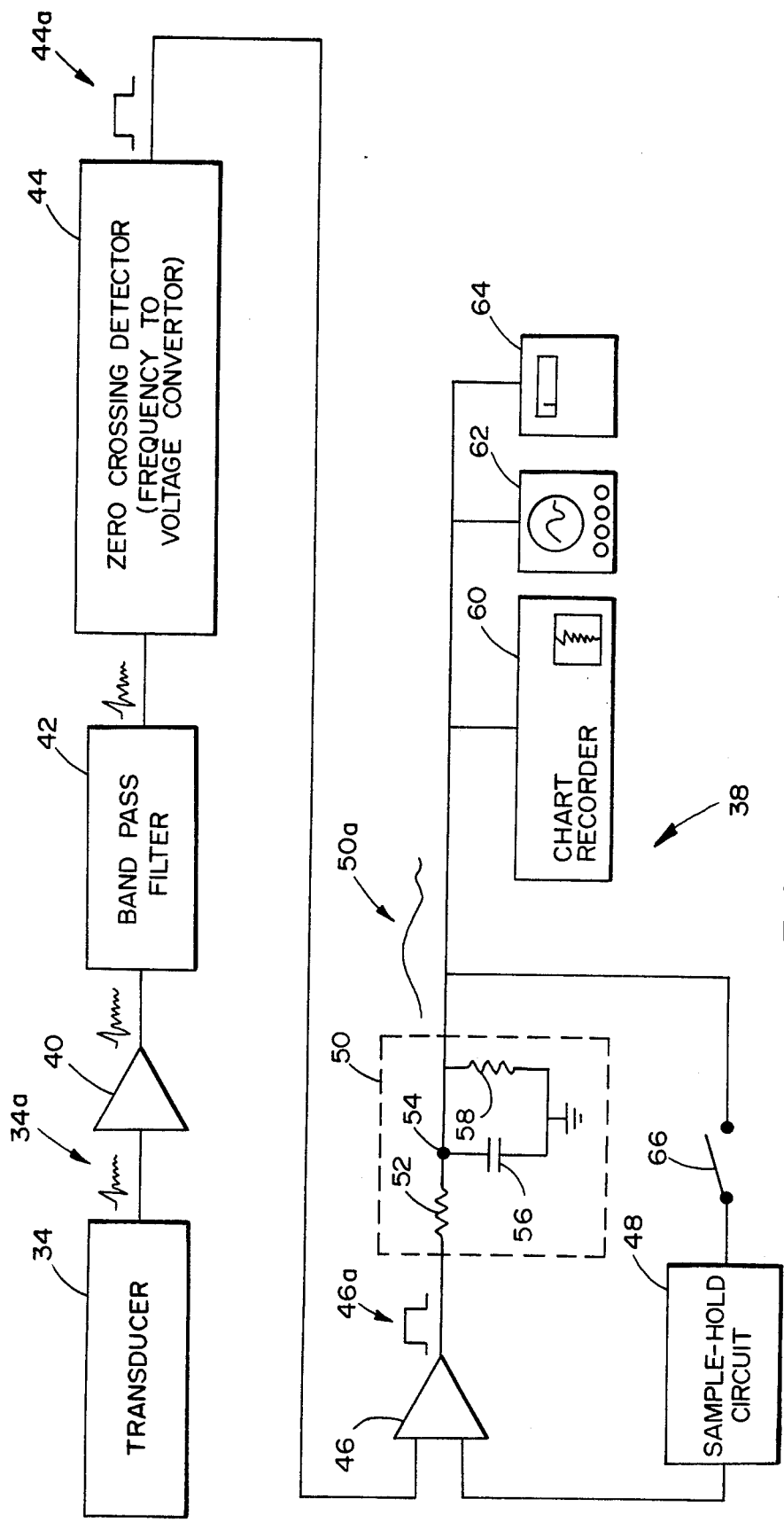
FIG. 4 illustrates, schematically, electrical circuitry for determining the pressure in a liquid.

Considering now a specific example of the signal processing means 38 suitable for converting the output signals from transducer 34 to a display or recording of pressure and pressure variations, if any, within the subject, reference should be made to FIG. 4. In response to an individual microbubble, transducer 34 generates an electrical output, depicted by waveform 34a in FIG. 4, which as previously discussed has a frequency indicative of the ambient pressure in the region of the microbubble. The waveform 34a of the transducer 34 is amplified by an amplifier 40 and transmitted through a band pass filter 42 to the input of a zero crossing detector 44. Band pass filter 42, which may be of known construction, suppresses wave trains having frequencies above or below those characteristic of the microbubbles and thus suppresses spurious data which could detract from the accuracy of the system.

Zero crossing detector 44 is of the known form which produces an output voltage, indicated by waveform 44a in FIG. 4, having a magnitude which is a function of the frequency of the input waveform. Thus the output of zero crossing detector 44 is a voltage having a magnitude indicative of the frequency of the sonic vibrations detected by transducer 34 in response to current microbubble production in the subject.

The output of zero crossing detector 44 is transmitted to one input of a differential amplifier 46, the other input of which receives a reference voltage from a sample and hold circuit 48 to be hereinafter discussed in more detail. Differential amplifier 46 transmits that portion of the waveform 44a which exceeds the reference voltage level to an integrating circuit 50 which may, for example, be an R-C network having a resistor 52 through which the output signals 46a of amplifier 46 are transmitted to a terminal 54. An integrating capacitor 56 and a second resistor 58 are connected in parallel between terminal 54 and ground. Integrating circuit 50 averages the amplitudes of the input waveforms 46a which are being received at any given time to produce an output voltage 50a which varies in accordance with variations of the average frequency of the waveforms 34a being generated by transducer 34. Where this average frequency varies over a period of time, as in the case of the blood pressure of a medical patient, for example, the output voltage 50a of integrating current 50 varies correspondingly.

Output voltage 50a from terminal 54 may be transmitted to any of a variety of display and/or receiving devices depending on the requirements of the specific usage of the invention. For example, the output of integrating circuit 50 may be connected to the input of a chart recorder 60 of the known form which produces a continuous graph on paper or the like corresponding to variations of an input voltage. The output voltage 50a from integrating circuit 50 may also be transmitted to the Y sweep frequency terminal of an oscilloscope 62 while a repetitive ramp signal is applied to the X sweep frequency terminal to generate a visible graphical display of pressure variations. Alternately or concurrently the output of integrating circuit 50 may be applied to a volt meter 64 suitably calibrated to indicate pressure. The various display or recording devices 60, 62 and 64 discussed above may be used individually or jointly and other forms of voltage indicator or recording device may also be used. As will be apparent, the output of integrating circuit 50 may also be stored by analog or digital means for later playback and display.

Sample and hold circuit 48, which provides the reference input to a differential amplifier or comparator 46, serves to maintain a reference signal. It also enhances accuracy of the data by eliminating that portion of the output signals 44a from zero crossing detector 44 which may result from background noise detected by transducer 34 or which may result from variations in ambient conditions that alter the frequency of the output wave trains 34a from transducer 34 in ways which are not indicative of the actual pressure which it is desired to measure. For example, the blood pressure of a medical patient may be affected by variations of barometric pressure and this will affect the frequency of the output wave trains 34a of transducer 34 although this component of the detected data is not medically significant. In order to remove these components of the pressure signals, or other components which may not be significant in other usages of the invention, sample and hold circuit 48 has an input which may be selectively connected to the output of integrating circuit 50 through a switch 66. Prior to making the measurement of the pressure which is to be detected, and prior to the initiation of microbubble production, switch 66 is temporarily closed to provide an input voltage to sample and hold circuit 48. The magnitude of such input voltage at that time is indicative of the background noise and background pressure effects. Sample and hold circuit 48 is of the form which detects the background input voltage while switch 66 is closed and then stores that data after the switch 66 is opened. After switch 66 is opened and the desired pressure measurement is in progress, hold circuit 48 applies the stored background voltage signal to the reference input of amplifier 46. Differential amplifier 46 then reduces the amplitudes of the output signals from zero cross detector 44 by an amount proportional to the magnitude of the background voltage signal to remove the unwanted components from the pressure readings.

The signal processing system 38 as described above is of an analog form for purposes of example. As will be apparent to those skilled in the art, the output of amplifier 40 may be transmitted to an analog to digital converter and the several subsequent functions of the system as described above may then be performed by equivalent digital data processing means, although a digital to analog converter must then be provided at the inputs to the display or recording devices 60, 62, 64 unless such devices are of the form which contain such converters internally or are digital devices themselves.

Calibration of the system against particles 26 which dissolve in a liquid of a known pressure, for example atmospheric pressure, provides a direct readout of main pulmonary artery 20 pressure against time since the frequency measured is determined from the equation:

$$P_{Pulmonary\ Artery} = (f_{meas} - f_0)/K$$

where K is a function of the particular gas in hollow space 30 and the diameter of the microbubble produced by release of that gas, $f_0$ is the frequency at ambient pressure, and $P_{Pulmonary\ Artery}$ is the pressure in the pulmonary artery at any time.

It should be pointed out that while the preferred gas is carbon dioxide, other gases can also be included in place of the carbon dioxide or in addition thereto. Other gases which are useful include nitrogen, oxygen, argon, xenon, air, methane, freon, ether and even carbon monoxide, so long as it is used in an amount that will not be harmful. It is of course important that whatever gas is utilized not be harmful to a living test subject when it is dissolved in the cardiovascular system.

The aforementioned and described method is useful for determining blood pressure, particularly in the main pulmonary artery, but also in other portions of the cardiovascular system. Such determination can be made without the utilization of a blood pressure cuff and without injuriously catheterizing the test subject.

The microbubbles, as formed in the manner just described, also serve to provide an enhanced ultrasonic image which provides useful diagnostic data to a physician. Also, substantially instantaneous blood flow rate can be determined by examining the ultrasonic image produced as described above and generated opposite a location in a patient's cardiovascular system. Both the positions and generally simultaneous velocities, when the microbubbles are of generally a uniform size, are measured to provide a determination of such blood flow rate. The velocity can be determined by observing the positions of the various microbubbles as a function of time. Previously mentioned copending application Ser. No. 36,098 describes such methods utilizing microbubbles in general, in more detail and that application is hereby incorporated herein by reference thereto.

While the invention has been described in terms of its use in a cardiovascular system, it should be apparent that it is also useful without modification to measure pressure in any liquid containing vessel.

Other aspects, objects, and advantages of this invention can be obtained from a study of the drawings, the disclosure and the appended claims.

I claim:

1. A method of determining pressure within a liquid containing vessel, comprising:
    adding a solid microbubble precursor to said liquid;
    retaining said precursor in said liquid for sufficient time to form a plurality of microbubbles thereby generating a plurality of sonic signals, said precursor forming said plurality of microbubbles at a plurality of times, wherein said precursor is formed to provide each of said microbubbles of a substantially equal selected size, said size being selected to be within a range from about 0.5 micron to about 325 microns;
    measuring a characteristic of said sonic signals representative of the pressure in the liquid, said measuring being of the ultrasonic frequency generated by formation of said microbubbles as a function of said times; and
    determining the pressure in the liquid from the measured characteristic, said determining being of the pressure in the liquid as a function of time.

2. A method as in claim 1, wherein said vessel is a cardiovascular system of a living being.

3. A method as in claim 1, wherein said vessel is a cardiovascular system of living test subject and said determined pressure include the systolic and the diastolic pressures of the living being.

4. A method as in claim 1, wherein said solid bubble precursor comprises at least one particle having a hollow space completely enclosed therein, said space being filled with a gas at a pressure above the pressure in said vessel, wherein said retaining is for a time sufficient to dissolve sufficient of said particles to allow said gas to escape from said hollow space and alternately expand and contract under the lesser pressure in said vessel towards an equilibrium bubble size and shape at said lesser pressure, and wherein said sonic signal is generated by said alternate expansion and contraction.

5. A method as in claim 1, wherein said particle is formulated of saccharide materials.

6. A method as in claim 5, wherein said vessel is a cardiovascular system of a living test subject and said determined pressure include the systolic and diastolic pressures of said living being.

7. A method of obtaining the substantially instantaneous volumetric flow rate in a cardiovascular system of a living being, comprising:
    adding a solid microbubble precursor to said system;
    retaining said precursor in said system for sufficient time to form a plurality of microbubbles and thereby generate a plurality of ultrasonic signals opposite a location in said system, each of said microbubbles being of a size within a range from about 0.5 micron to about 325 microns;
    obtaining an ultrasonic image representative of said ultrasonic signal, said image simultaneously providing a measurement of both the positions and velocities of said microbubbles opposite said location; and
    determining the substantially instantaneous volumetric flow rate at said location from said image.

8. A method as in claim 7, wherein said microbubbles are of generally a uniform size.

9. A method of enhancing ultrasonic echographic imaging in a liquid enclosed in a vessel by increasing image contrast, comprising:
    adding a solid microbubble precursor to said liquid;
    retaining said precursor in said vessel for sufficient time to form a plurality of microbubbles in said liquid, each of said microbubbles being of a size within a range from about 0.5 micron to about 325 microns; and
    obtaining an enhanced ultrasonic echographic image of said liquid opposite a position therein containing said microbubbles by increasing the relative contrast between said liquid and said vessel.

* * * * *